US011583448B1

(12) United States Patent
Arsenault (10) Patent No.: US 11,583,448 B1
(45) Date of Patent: Feb. 21, 2023

(54) EYEWEAR ACCESSORY (71) Applicant: Peter Arsenault, Dracut, MA (US)

(72) Inventor: Peter Arsenault, Dracut, MA (US)

(*) Notice: Subject to any disclaimer, the term of this patent is extended or adjusted under 35 U.S.C. 154(b) by 375 days.

(21) Appl. No.: 16/106,447

(22) Filed: Aug. 21, 2018

Related U.S. Application Data (60) Provisional application No. 62/605,843, filed on Aug. 31, 2017.

(51) Int. Cl.
*A61F 9/04* (2006.01)
*A61C 19/00* (2006.01)
*A41D 13/11* (2006.01)

(52) U.S. Cl.
CPC .............. *A61F 9/045* (2013.01); *A61C 19/00* (2013.01); *A41D 13/1184* (2013.01)

(58) Field of Classification Search
CPC A41D 13/1184; A41D 13/11; A41D 13/1611; A41D 13/1169; A41D 13/1176; A41D 13/1107; A41D 13/1115; A41D 13/1123; A41D 13/113; A41D 13/1138; A41D 13/1153; A61F 2013/00476; A61F 9/04; A61F 9/045; A61F 9/025; A61F 9/029; A61F 2013/00361; A61F 2013/00365; A62B 23/06; A45D 44/002; A45D 44/12
USPC .......................................... 128/857–858, 863
See application file for complete search history.

(56) References Cited

U.S. PATENT DOCUMENTS

| | | | |
|---|---|---|---|
| 3,974,829 A * | 8/1976 | Tate, Jr. ............. | A41D 13/1115 128/201.17 |
| 4,797,956 A | 1/1989 | Boyce | |
| 5,150,703 A * | 9/1992 | Hubbard ............ | A41D 13/1184 128/201.17 |
| 6,079,980 A | 6/2000 | Durand | |
| 6,185,740 B1 * | 2/2001 | Zegarelli ................. | A61F 9/045 128/857 |
| 6,532,598 B1 | 3/2003 | Cardarelli | |
| 7,077,137 B2 * | 7/2006 | Russell .................. | G02C 11/00 128/201.12 |
| 7,540,039 B2 | 6/2009 | Reaux | |
| 8,240,302 B1 | 8/2012 | Tayebi et al. | |
| 2006/0143766 A1 | 7/2006 | Ramsey | |
| 2008/0143953 A1 * | 6/2008 | Welchel ................. | G02C 11/08 351/158 |
| 2011/0271955 A1 * | 11/2011 | Palomo .............. | A41D 13/1115 128/206.16 |

(Continued)

FOREIGN PATENT DOCUMENTS

WO WO1989010106 A1 11/1989

*Primary Examiner* — Rachael E Bredefeld
*Assistant Examiner* — Trisha Talapatra
(74) *Attorney, Agent, or Firm* — Bradley K. DeSandro; DeSandro Law Group PLLC (57) ABSTRACT

A patient safety shield, and its method of use, features a deflector shield that closes gaps between the bottom profile of safety eyewear worn by the patient and the patient's cheek area. The deflector shield, when positioned, oriented, and profiled across the bridge of the patients nose and under the patient's eyewear, deflects fine infectious and or injurious debris, which originates in the patient's oral cavity, from being ejected off moving parts of dental tools during a dental procedure. The deflection by the deflector shield prevents potentially infectious or injurious debris from reaching and harming the eyes of the patient that may enter through the bottom gaps.

18 Claims, 5 Drawing Sheets

(56) References Cited

U.S. PATENT DOCUMENTS

| | | |
|---|---|---|
| 2012/0222185 A1 | 9/2012 | Erikson |
| 2016/0015098 A1* | 1/2016 | Conlon |
| 2017/0027251 A1* | 2/2017 | Kang ................. A41D 13/1184 |
| 2017/0095015 A1* | 4/2017 | O'Leary ............... A62B 18/082 |
| 2018/0263309 A1* | 9/2018 | Mendez ............. A41D 13/1107 |

* cited by examiner

EYEWEAR ACCESSORY

CROSS REFERENCE TO RELATES APPLICATIONS

This application claims priority to Provisional Application Ser. No. 62/605,843, titled "Patient Safety Deflector Shield To Close Bottom Gaps For Use With Safety Glasses In A Dental Setting," filed on Aug. 31, 2017, which is incorporated herein by reference.

FIELD

Implementations generally relate to the field of protection of the eyes of a dental patient who is inherently exposed to air-borne fine-size particulate debris and projectiles which may impact and harm the patient's eyes during a dental care procedure provided by a dental professional such as a dentist, dental assistant, dental hygienist, or other practitioner.

BACKGROUND

While undergoing dental treatment of a dental care provider, a patient should wear appropriate eye protection. Lenses in a patient's protective eyewear with side shields are helpful, particularly in consideration of: (i) the spatial relationship of the dental care provider and the patient; and (ii) the use of high and low speed rotary instruments and dental instrumentation by the dental care provider in the patient's oral cavity. This spatial angulation and dental instrument activity may result in projectiles off of the dental instruments reaching the patient's eyes by traveling vertically and tangentially through gaps which result between the patient's cheeks and the respective lower rims of the lenses of the patient's protective eyewear. Infection and injury may result when projectiles reach the patient's eyes. As such, it would be an advantage in the dental health care provider arts to provide a patient safety shield to close open bottom gaps between the patient's cheeks and the lower rims of the lenses of the patient's protective eyewear, thereby preventing potential infection and injury.

SUMMARY

In one implementation, a patient wears eyewear having two lenses in a frame or frameless protective eyewear. The eyewear has a width. Bottom gaps are formed respectively between the left and right cheeks of the patient and below the bottom edge of the patient's protective eyewear. A patient safety shield is placed across the patients nose and is configured as to close the generated bottom gaps. The patient safety shield includes a first, flexible and compressible, material having a length at least the width of the frame, and a folding region across the length of the shield. Also included is a second material attached to, and not exceeding the length of, the first material. The second material is bendable from a first position thereof to a second position thereof. The second material, after being bent, retains the second position thereof and causes the first material, after being bent with the first material from a first position thereof to a second position thereof, to also retain the second position thereof. The second positions of the first and second material make a conforming fit over both the nose of the person and the left and right cheek portions of the person adjacent to the nose of the person. The patient safety shield also includes a deflector shield, having left and right portions, contiguous to the first material at the folding region. When: (i) the patient safety shield is worn by the patient across the nose of the patient; (ii) the safety shield is folded at the folding region or score line into a plane approximately normal to a plane assumed by the deflector shield; and (iii) the safety shield (deflector shield) are bent from the respective first positions thereof to the second positions thereof so as to make conforming fits over both the nose of the patient and the left and right cheek portions of the patient adjacent to the nose of the patient; then (vi) the left and right portions of the deflector shield respectively cover over the left and right gaps that are formed respectively between the left and right cheeks of the patient and below the patient's eyewear.

In another implementation potential eye infection or injury is prevented for a patient wearing safety glasses or eyewear incident to a dental procedure. The eyewear has left and rights lenses in a frame or are frameless. Left and right bottom gaps are formed respectively between the left and right cheeks of the patient and below left and right bottom portions of the patient eyewear. A patient safety shield is placed across the bridge of the patients nose and below the left and right lenses of the patient's eyewear. The patient safety shield has a facial contact portion that has a deflector shield that extends from a periphery thereof. The deflector shield has left and right portions. The patient facial contact portion is first bent into a plane approximately normal to a plane assumed by the deflector shield. The patient facial contact portion is then bent from a first position thereof to a second position thereof. The patient safety shield, after being bent, retains the second position thereof. The second position of the patient safety shield causes the facial contact portion of the patient safety shield to make a conforming fit about the nose of the patient and the left and right cheek portions of the patient adjacent to the nose. When so worn by the patient, the left and right portions of the deflector shield respectively close the left and right bottom gaps that are formed respectively between the left and right cheeks of the patient and below the bottom edge of the patient eye wear.

In an alternative embodiment of the foregoing implementations, the patient safety shield is positioned across the bridge of the nose of the patient and dental treatment is performed in the oral cavity of the patient. The dental treatment may result in projectiles and aerosol sprays that may be hazardous and infectious originating from the oral cavity of the patient. However, the left and right portions of the deflector shield deflect the projected, potentially infectious material from making contact with either or both of the patient's eyes by respectively covering over the left and right bottom gaps that are formed respectively between the left and right cheeks of the patient and below the patient's eyewear.

BRIEF DESCRIPTION OF THE DRAWINGS

Implementations will become more apparent from the detailed description set forth below when taken in conjunction with the drawings, in which like elements bear like reference numerals.

DETAILED DESCRIPTION

Figure 4:
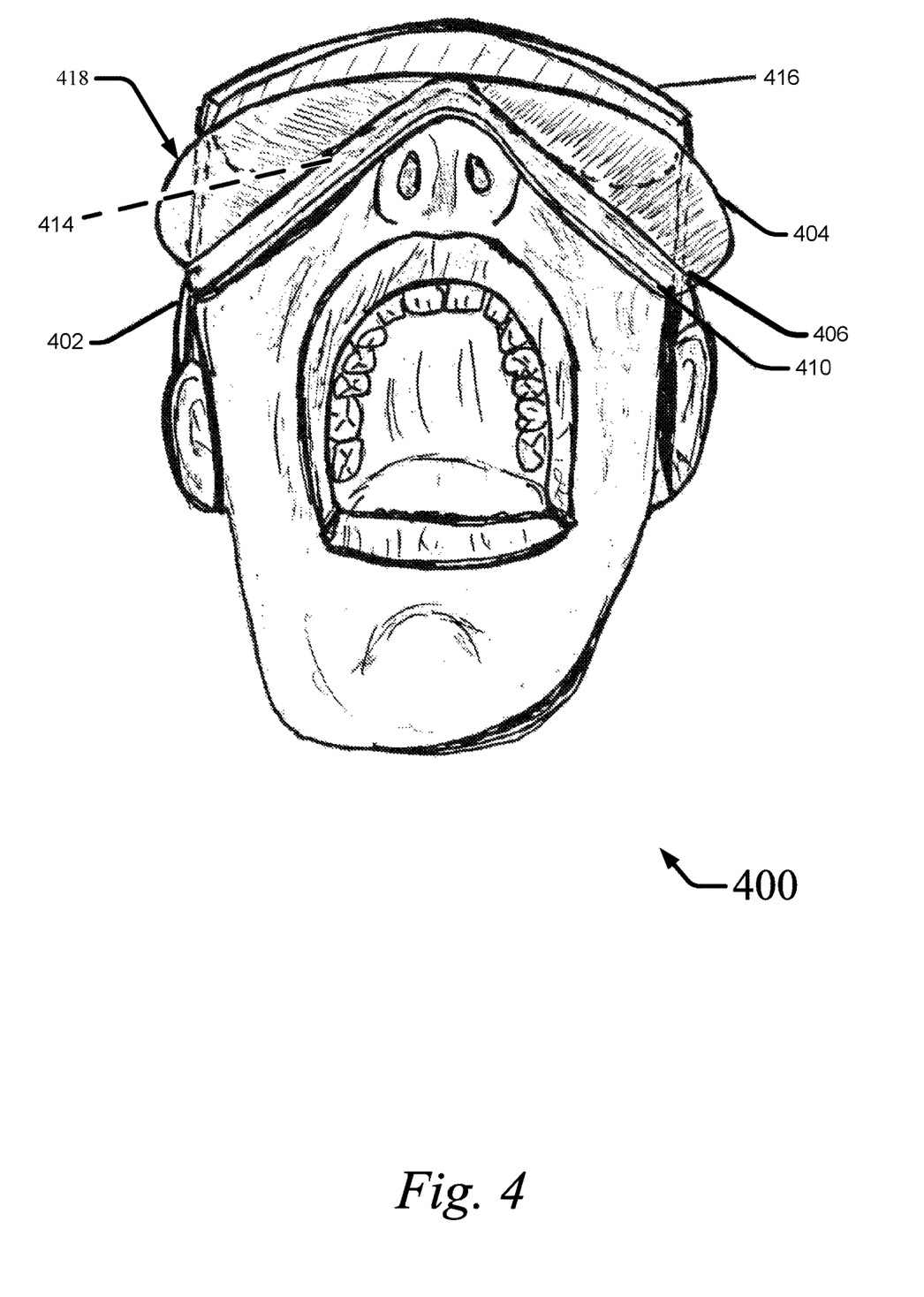
FIG. 4 is a front elevational view of a patient's head and face, where the patient's head and face are shown to be wearing safety eye wear below which an exemplary patient safety shield is worn by the patient, where the exemplary patient safety shield has a deflector shield and a comfort foam strip, where the patient is shown with the patient's mouth open and safety glasses in place, and where the deflector shield portion and comfort foam strip has been folded about a perforated score line in the exemplary patient safety shield so as to make a conforming fit to both the patient's nose and the patient's face portions adjacent to the patient's nose.
Figure 5:
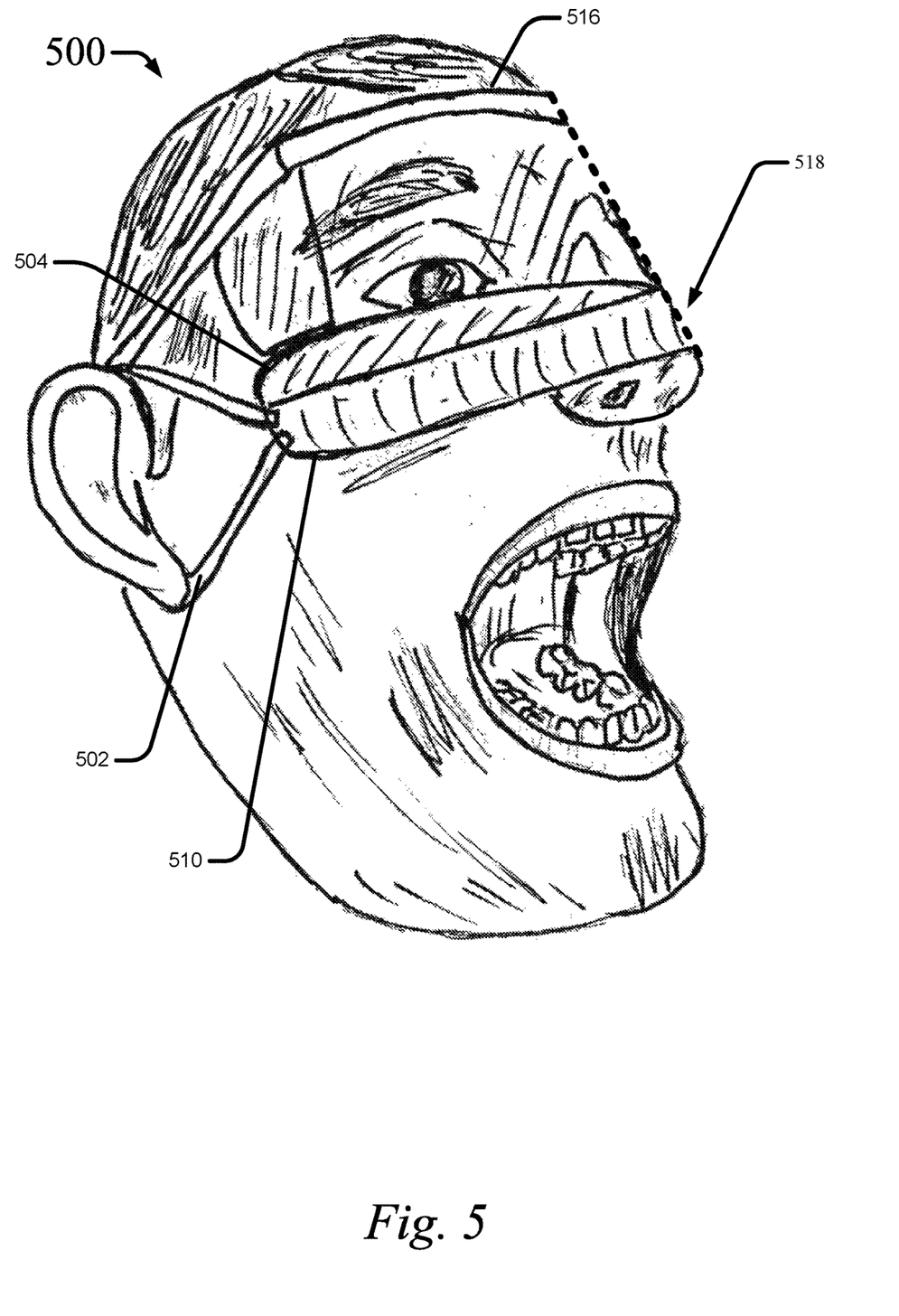
FIG. 5 is a perspective view of FIG. 4 cutaway to show approximately only the right side of the patient's face.

Implementations relate to a patient safety shield for patient use in a dental setting. The patient safety shield, when worn below a patient's safety eye wear, such as safety glasses, and across the bridge of the patient's nose, closes each of the two (2) bottom gaps below the patient's safety glasses. Each of the two (2) bottom gaps are an open space that exists between the lower edge of the patient's safety eyewear and the patient's cheeks. The patient safety shield will preferably be used below and in combination with standard safety eyewear as shown in FIGS. 4-5. The patient safety shield may be used in dental/medical applications and other settings where bottom gap eye protection would be appropriate.

Figure 1:
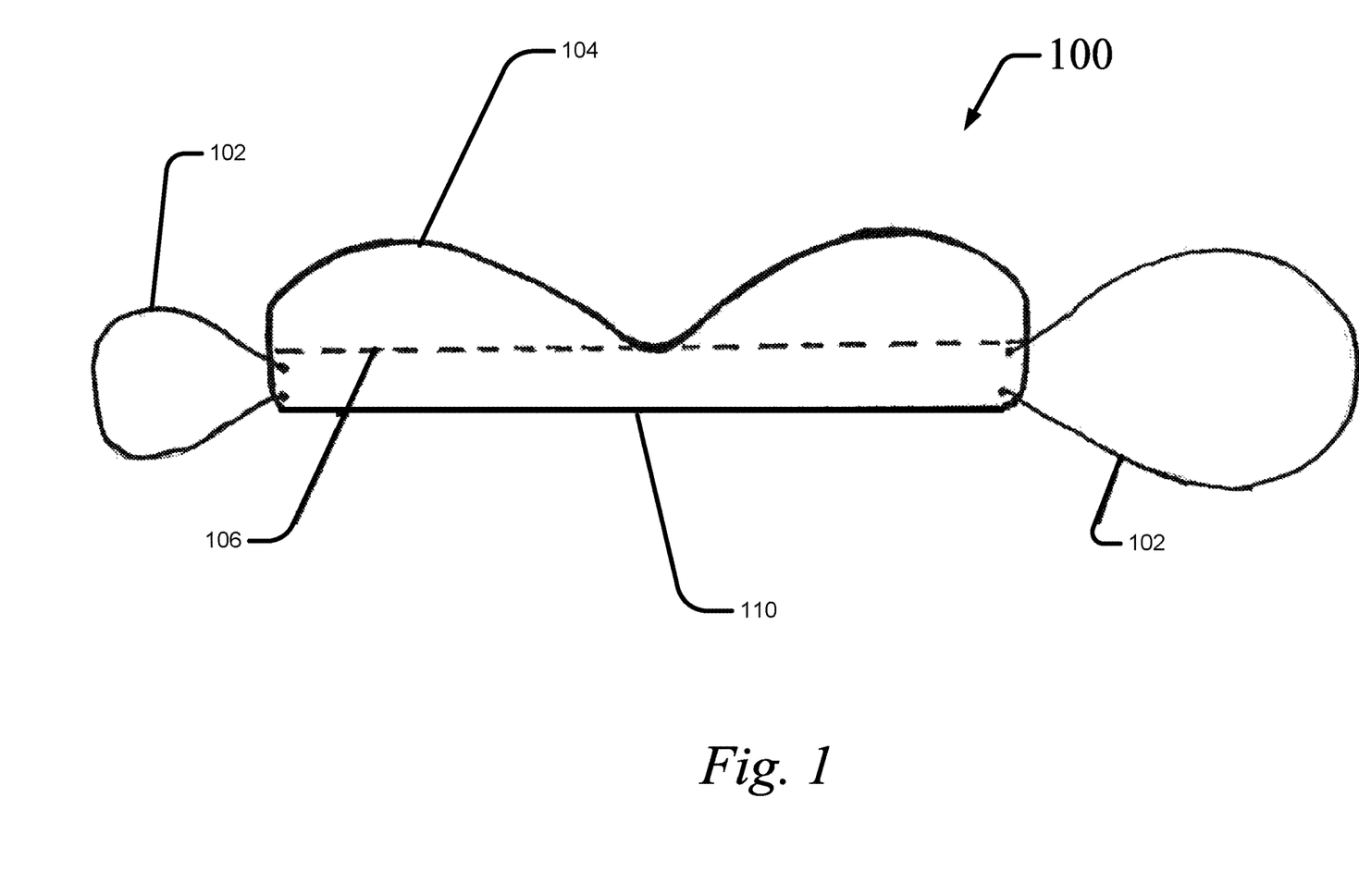
FIG. 1 is a top view of an exemplary patient safety shield having a deflector shield and a comfort foam strip shown within the same plane and showing a perforated score line which allows the deflector shield to be folded out of the same plane to an approximate 90-degree orientation with respect to the unfolded deflector shield portion and comfort foam strip.
Figure 2:
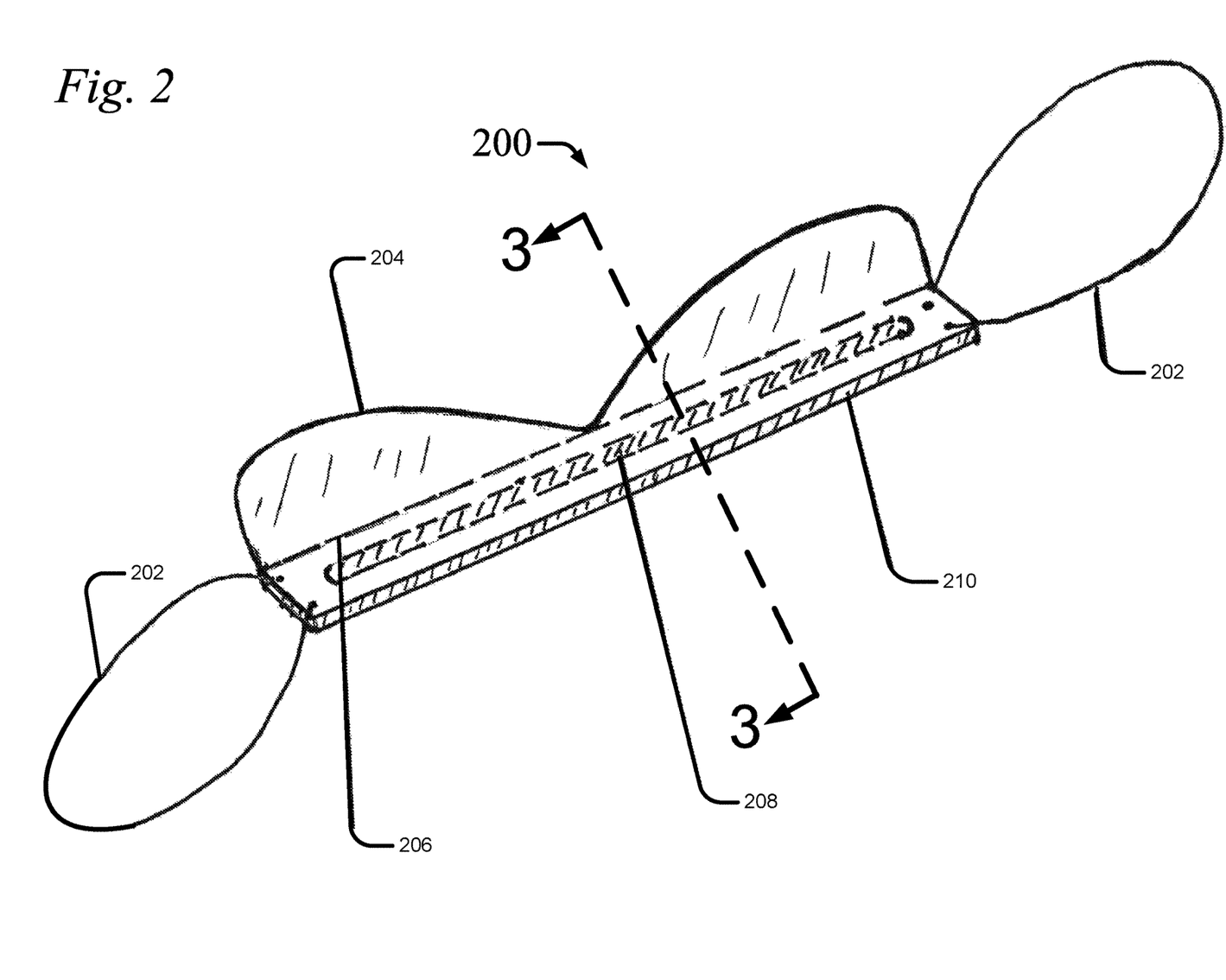
FIG. 2. is a perspective view of an exemplary patient safety shield having a deflector shield and a comfort foam strip shown to be folded along the perforated score line which allows the deflector shield to be folded to an approximate 90 degree orientation (e.g., normal to) with respect to the unfolded deflector shield portion and comfort foam strip.
Figure 3:
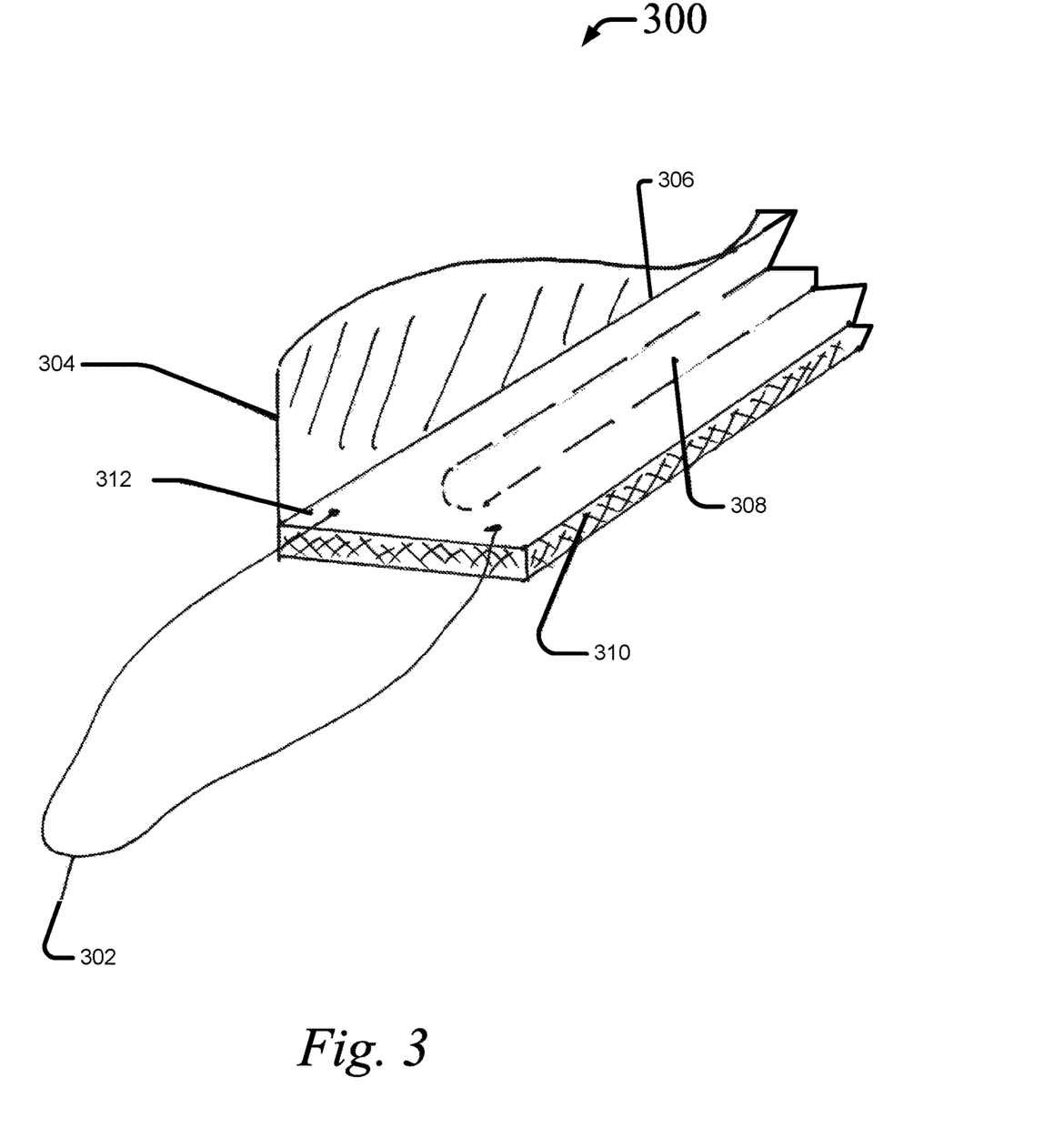
FIG. 3 is a cutaway perspective view taken along the 3-3 Section seen in FIG. 2 after the patient safety shield has been adjusted into a position thereof in which the deflector shield is folded to an approximate 90-degree orientation with respect to the unfolded deflector shield portion and comfort foam strip by way of the perforated score line.

FIGS. 1 and 3 shows an exemplary implementation of a patient safety shield 100 having elastic ear loops 102, a deflector shield 104, a bendable nose clip 308, and a comfort foam strip 310. Deflector shield 104 has right and left portions each of which will preferably be an identical mirror-image of the other so as to be similarly profiled, oriented, and attached. Nose clip 308 will preferably be bendable and retains its shape after being bent. Comfort foam strip 310 is also bendable but does not retain its shape after being bent but for the presence of nose clip 308 which is either embedded within (as shown in FIGS. 2-3) or mounted upon (not shown in FIGS. 2-3) comfort foam strip 310. Deflector shield 104 will preferably be composed of a base material such a plastic, Mylar® (e.g., polyester), or other material having a functional equivalent thereof including functional paper product and additionally, various polymeric materials. The deflector shield 104 will preferably have a thickness of approximately 0.005 inches, although other implementations may vary in thickness as required by design. The base material will preferably be polymeric in nature and can be a variety of polymeric materials as well and also a functional paper product if so indicated. The base material may be opaque, transparent, colored and or printable. The deflector shield 104 will preferably have a perforated score line 106 which allows the deflector shield to be folded to an approximate 90 degree orientation as illustrated and described herein.

In alternative implementations, deflector shield 104 can be made of: (i) at least a portion of a flexible material; (ii) at least a portion of a high impact material; (iii) at least a portion of a transparent material; (iv) at least a portion of an opaque material; (v) at least a portion of a translucent material; (vi) a monolithic construction; (vii) a material having two (2) separate components that are respectively left and right segments; (viii) a material that is bendable relative to the comfort foam strip 310 such as along the perforated score line 106; or (ix) a combination of the foregoing.

When the deflector shield 104 is folded along the perforated score line 106, as shown and described herein, the patient safety shield 100 will preferably be placed and fitted on the patient's face across and over the bridge of the patient's nose and face so as to cover over the bottom gaps or lower edge of the patient's eyewear as will be described below with respect to FIGS. 4-5. Folding the deflector shield 104 along the perforated score line 106 allows the portions above the perforated score line 106, which are shaped as bilateral lobes, to act as portions that deflect particulate matter when the patient safety shield 100 is properly worn. These lobes are designed to cover over the bottom gaps or lower edge of the patient's eyewear as will be described below with respect to FIGS. 4-5.

The deflector shield 104 will preferably be attached to a comfort form strip 310. The comfort foam strip 310 will preferably have a nose clip strip 308 embedded within or secured upon the comfort foam strip 310. The nose clip strip 308 will preferably be composed of a material that can be shaped so as to cause the comfort foam strip 310 to conform to the patient's facial geometry. By way of example, the nose clip strip 308 can be formed of aluminum, other bendable material, or it's functional equivalent. The deflector shield device 104 is attached to the comfort foam strip 310. The comfort foam strip 310 can vary in thickness and be applied to the underside of that portion of the deflector shield 104 that contacts the patient's face as will be described below with respect to FIGS. 4-5.

The nose clip strip 308 is preferably applied between the bottom portion of the deflector shield 104 and between the comfort foam strip 310 so as to hide the nose clip strip 308 and to protect the patient's face from abrasion. With the comfort foam strip 310 as such, its location thus provides a comfortable interface between the patient safety shield 104 and the patient's face as will be described below with respect to FIGS. 4-5.

The comfort foam strip 310 and the nose clip strip 308 may both be attached, such as with an adhesive, heat staked, or welded to the back side of the deflector shield 104.

The patient safety shield 100 has a pair of elastic ear loops 102 which are attached to both sides of the patient safety shield 100 in order for the patient safety shield 100 to be held in place on the patient's face as will be described below with respect to FIGS. 4& 5 The pair of elastic ear loops 102 are attached to the patient safety shield 100, such as by way of staples, adhesive, ultrasonically welding, and the like.

FIG. 2 shows a perspective view of an exemplary patient safety shield 200 having a deflector shield 204 and a comfort foam strip 210. Both deflector shield 204 and comfort foam strip 210 are shown in FIG. 2. Also seen in FIG. 2 are a perforated score-line 206, a pair of elastic ear loops 202, a comfort foam strip 210 attached to a deflector shield 204, and a nose clip 208 which may be composed of a bendable material such as aluminum or its functional equivalent. In FIG. 2, the perforated score-line 206 allows the deflector shield 204 to be folded out of the same plane to an approximate 90 degree orientation with respect to the comfort foam strip 210.

An illustration taken about the 3-3 Section seen in FIG. 2 is shown in FIG. 3 as a cutaway perspective view of a patient safety shield 300. Like the patient safety shield 200 seen in FIG. 2, the patient safety shield 300 has been adjusted into a position thereof in which a deflector shield 304 has been folded to an approximate 90-degree orientation with respect to a comfort foam strip 310 by way of a perforated score line 306. As such, the patient safety shield 300 is depicted so as to show a "sandwiching" of a nose clip 308 in relation to the comfort foam strip 310. An elastic ear loop 302 has attachments as shown to the shield body with the comfort foam strip contained within the sandwich 310.

Referring now to FIG. 4, a patient 400 is shown. In FIG. 4, the patient's 400 head and face are shown to be wearing safety eyewear 416 over which an exemplary patient safety shield 418 is worn by the patient. The patient safety shield 418 has a deflector shield 404 and a comfort foam strip 410. Patient 400 is shown with the patient's 400 mouth open and safety glasses 416 in place. The comfort foam strip 410 has been folded about a perforated score line 406 so as to make a conforming fit to both the patient's 400 nose and the patient's 400 face portions adjacent to the patient's nose, thereby covering over bottom gaps 414 on opposing sides of the patient's 400 nose. Patient 400 is depicted with open mouth and head tilted back as would be positioned in a typical dental setting with safety eyewear 416 in place. This view illustrates the patient safety shield 418 conforming to the patient's 400 face with a perforated score line 406 and nose clip (not shown) formed and being held in position with two (2) elastic ear loops 402 on each of the patient's 400 ears. FIG. 4 shows that two (2) opposing lobes of the deflector shield 404 respectively cover over and thereby close the two (2) bottom gaps 414 when the patient safety shield 418 shield is worn as illustrated in FIGS. 4-5.

Referring now to FIG. 5, a cutaway view shows approximately only the right side of a patient's 500 face in perspective. The patient 500 is shown wearing a patient safety shield 518 which includes a pair of elastic ear loops 502 of which only the right elastic ear loop 502 is shown in FIG. 5, a comfort foam strip 510, a deflector shield 504, and a nose clip (not shown) embedded within comfort foam strip 510. Patient 500 is shown with the patient's 500 mouth open and safety eye wear 516 in place. As shown in FIG. 5, patient safety shield 518 has covered over and effectively closed the two (2) bottom gaps between safety eye wear 516 and the patient's 500 cheeks due to proper wear orientation and location of patient safety shield 518.

In respective alternative implementations of FIGS. 1-5, ear loops 102, 202, 302, 402, and 502 are optional and the function provided thereby may be replaced by other means for adhering patient safety shield 100, 200, and 300 to the patient's face 400, 500. By way of example and not by way of limitation, such a patient facial adherent can be facilitated by: (i) two (2) pieces of tape attached to opposing sides of the patient safety shield, where each piece of tape has an adhesive on opposing sides thereof so as to respectively adhere to the patient's face on one side thereof and to adhere to the patient safety shield on the opposing side thereof; (ii) two (2) pieces of tape attached to opposing sides of the patient safety shield, where each piece of tape has an adhesive on one side thereof, where the tape is adhered to one side of the patient's face at one end thereof and is adhered to the patient safety shield on the opposing side thereof; (iii) an adhesive bandage, with or without a gauze pad in the center thereof which is typically used to cover minor abrasions (e.g., Band-Aid® adhesive bandage) but is used in one implementation to adhere the patient safety shield to the patient's face; (iv) an adhesive or glue, preferably biologically inert and hypoallergenic, that is topically applied to at least one of the patient's face and the patient safety shield 100, 200, 300, 400 and 500; and (v) a combination of the foregoing.

Safety glasses 416, 516 respectively seen in FIGS. 4-5, as is typical of eye wear, have a nose bridge-contacting portion and left and right cheek side area-contacting portions, where the left and right segments respectively contact the left and right sides of the nose of the patient, and also contact the left and right cheek upper areas of the patient's face. Also as is typical of eye wear, two (2) gaps are respectively generated between left and right bottom profile of safety eye ware 416, 516 and respective left and right upper portions of the patient's cheek area. When patient safety shield 418, 518 is properly installed over safety glasses 416, 516, the left and right portions of deflector shield 404, 504 will respectively cover the left and right gaps generated between the patient's left and right cheeks and the left and right bottom profile of a protective eyewear 416, 516. As such, the two (2) gaps are effectively closed so as to provide effective eye or face protection against hazards from flying spatter, flying liquids, flying particular matter, flying particulate bearing liquids, etc., whether infectious or not, which flying eye or face hazards would otherwise enter through the two (2) gaps between the lower rims of the patient's eyewear or safety glasses lenses 416, 516 and the respective two (2) patient's cheek areas.

A healthcare provider in a dental setting will preferably ensure that each patient be provided appropriate eye or face protection when exposed to eye or face hazards from flying spatter, flying liquids, flying particular matter, flying particulate bearing liquids, etc. In addition to safety glasses, adjunct eye protection as described and illustrated herein with respect to a patient safety shield provides an effective means of eye or face protection by way of deflecting air-borne debris and other hazards such as flying spatter, flying liquids, flying particular matter, flying particulate bearing liquids, etc., whether infectious or not, which flying eye or face hazards would otherwise, but for such deflection, potentially could enter through one or both of the two (2) gaps between the lower rims of the patient's safety glasses lenses and the respective two (2) patient's cheek areas.

Reference throughout this specification to "one example", "an example", "certain examples", or "exemplary implementation" means that a particular feature, structure, or characteristic described in connection with the feature and/or example may be included in at least one feature and/or example of claimed subject matter. Thus, the appearances of the phrase "in one example", "an example", "in certain examples" or "in some implementations" or other like phrases in various places throughout this specification are not necessarily all referring to the same feature, example, and/or limitation. Furthermore, the particular features, structures, or characteristics may be combined in one or more examples and/or features.

While there has been illustrated and described what are presently considered to be example features, it will be understood by those skilled in the art that various other modifications may be made, and equivalents may be substituted, without departing from claimed subject matter and spirit and scope. Additionally, many modifications may be made to adapt a particular situation to the teachings of claimed subject matter without departing from the central concept described herein. Therefore, it is intended that claimed subject matter not be limited to the particular examples disclosed, but that such claimed subject matter may also include all aspects falling within the scope of appended claims, and equivalents thereof.

In the preceding detailed description, numerous specific details have been set forth to provide a thorough understanding of claimed subject matter. However, it will be understood by those skilled in the art that claimed subject matter may be practiced without these specific details. In other instances, methods and systems that would be known by one of ordinary skill have not been described in detail so as not to obscure claimed subject matter.

What is claimed is:

1. A dental patient eyes safety shield accessory for eyewear having left and right lenses and configured to be worn by a dental patient for protection of the eyes of the dental patient inherently exposed to aerosol sprays and flying air-borne fine-size particulate debris and projectiles originating from the uncovered oral cavity of the dental patient which may impact and harm the eyes of the dental patient during a dental care procedure provided by a dental professional, wherein left and right gaps are configured to form respectively between the left and right cheeks of the dental patient wearing the eyewear and below the left and right lenses of the eyewear, and wherein the dental patient eyes safety shield accessory comprises:

a first material being substantially flexible and compressible;

a second material attached to, and not exceeding the length of, the first material, the second material being bendable from a first position thereof to a second position thereof, wherein:

the second material, after being bent, retains the second position thereof and causes the first material, after being bent with the second material, to bend from a first position thereof to a second position thereof that is also retained with the second position of the second material;

the second material is positioned below the left and right lenses of the eyewear; and the second position of the first material is configured to make a conforming fit over and in contact with both:
the nose of the dental patient; and
the left and right cheek portions of the dental patient adjacent to the nose of the dental patient;

and a deflector shield, having left and right portions, attached to:
the first material; and
ear loops configured to be fitted over or around the ears of the dental patient;

wherein the dental patient eyes safety shield accessory for eyewear is configured to be worn by the dental patient and overlaps the eyewear worn by the dental patient and is neither attached, connected, nor adhesively bound to the eyewear worn by the dental patient, whereby:

when the ear loops are fitted over or around the ears of the dental patient, then the dental patient eyes safety shield accessory is held in place and against the face of the dental patient;

and when:
the dental patient eyes safety shield accessory is worn by the dental patient below the eyewear worn by the dental patient;
the first material is folded into a plane approximately normal to a plane assumed by the deflector shield; and
the first material and the second material are bent from the respective first positions thereof to the second positions thereof such that the first material is configured to make conforming fits over and in contact with both:
the nose of the dental patient; and
the left and right cheek portions of the dental patient adjacent to the nose of the dental patient;

then:
the dental patient eyes safety shield accessory does not cover the oral cavity of the dental patient;
the left and right portions of the deflector shield do not substantially block:
the uncovered oral cavity of the dental patient;
the nostrils of the dental patient; and
a line of vision of the dental patient;
and the deflector shield deflects the aerosol sprays and flying air-borne fine-size particulate debris and projectiles from the uncovered oral cavity of the dental patient which may impact and harm the eyes of the dental patient during the dental care procedure provided by the dental professional; the dental patient eyes safety shield accessory for eyewear does not cover the nostrils of the dental patient; and nothing is attached to a bottom or a posterior area of the dental patient eyes safety shield accessory for eyewear.

2. The dental patient eyes safety shield accessory for eyewear as defined in claim 1, wherein the first material is substantially formed by trapping pockets of gas in a liquid so as to form cells.

3. The dental patient eyes safety shield accessory for eyewear as defined in claim 1, wherein the first material is substantially composed of a solid foam material.

4. The dental patient eyes safety shield accessory for eyewear as defined in claim 1, wherein the second material is substantially malleable and ductile.

5. The dental patient eyes safety shield accessory for eyewear as defined in claim 1, wherein the second material is substantially composed of aluminum.

6. The dental patient eyes safety shield accessory for eyewear as defined in claim 1, wherein the first material can be folded into the plane that is approximately normal to the plane assumed by the deflector shield.

7. The dental patient eyes safety shield accessory for eyewear as defined in claim 1, wherein the right and left portions of the deflector shield are substantially mirror-images.

8. The dental patient eyes safety shield accessory for eyewear as defined in claim 1, wherein the second material has a surface on which the first material is attached.

9. The dental patient eyes safety shield accessory for eyewear as defined in claim 1, wherein at least a portion of the second material is embedded within the first material.

10. The dental patient eyes safety shield accessory for eyewear as defined in claim 1, wherein the deflector shield is configured to be conformable to fit to the face of the dental patient wearing the eyewear to protect the eyes of the dental patient, whereby the dental patient's eyes are protected from:
- perpendicular, frontal debris trajectory pathways; and
- side trajectory pathways.

11. A dental patient eyes safety shield accessory for eyewear having left and right lenses and configured to be worn by a dental patient for protection of the eyes of the dental patient inherently exposed to aerosol sprays and flying air-borne fine-size particulate debris and projectiles from the uncovered oral cavity of the dental patient which may impact and harm the eyes of the dental patient during a dental care procedure provided by a dental professional, the dental patient safety shield accessory comprising:
- a first portion having a length at least the width of the eyewear;
and
- a second portion connected to, and not substantially exceeding the length of, the first portion, wherein:
  - the first and second portions are flexible to make a conforming fit over and in contract with the nose of the dental patient;
  - the second portion is positioned below the left and right lenses; and
  - the first portion is flexible to make a conforming fit over and in contact with the left and right cheek portions that are adjacent to the nose of the dental patient;
and
- a deflector shield having left and right portions that:
  - do not substantially block:
    - the uncovered oral cavity;
    - the nostrils of the dental patient; and
    - a line of vision of the dental patient;
  - extend above the first portion respectively to the left and right lenses;
  - respectively cover left and right gaps formed respectively:
    - between the left and right cheeks of the dental patient; and
    - below the left and right lenses of the eyewear;
  - are attached to ear loops configured to be fitted over or around the ears of the dental patient;
wherein the dental patient eyes safety shield accessory for eyewear is configured to be worn by the dental patient and overlaps the eyewear worn by the dental patient and is neither attached, connected, nor adhesively bound to the eyewear worn by the dental patient, whereby
- when the ear loops are fitted over or around the ears of the dental patient, then the dental patient eyes safety shield accessory is held in place and against the face of the dental patient;
- the dental patient safety shield accessory does not cover the oral cavity of the dental patient;
and
- the eyes of the dental patient are protected from aerosol sprays and the flying air-borne fine-size particulate debris and projectiles from the uncovered oral cavity of the dental patient which may impact and harm the eyes of the dental patient during the dental care procedure provided by the dental professional; the dental patient eyes safety shield accessory for eyewear does not cover the nostrils of the dental patient; and nothing is attached to a bottom or a posterior area of the dental patient eyes safety shield accessory for eyewear.

12. The dental patient eyes safety shield accessory for eyewear as defined in claim 11, wherein:
- the first portion comprises at least one of:
  - a material substantially formed by trapping pockets of gas in a liquid so as to form cells; and
  - a material is substantially composed of a solid foam material; and
- the second portion comprises at least one of:
  - a material substantially malleable and ductile; and
  - a material is substantially composed of aluminum.

13. The dental patient eyes safety shield accessory for eyewear as defined in claim 11, wherein:
- the first portion can be folded into a plane that is approximately normal to a plane assumed by the deflector shield;
- the second portion has a surface on which the first portion is attached; and
- some of the second portion is embedded within the first portion.

14. The dental patient eyes safety shield accessory for eyewear as defined in claim 11, wherein the right and left portions of the deflector shield are substantially identical mirror-image of the other so as to be similarly profiled, oriented, and attached.

15. The dental patient eyes safety shield accessory for eyewear as defined in claim 11, wherein:
- the deflector shield is configured to be conformable to fit to the face of the dental patient wearing the eyewear; and
- when the dental patient eyes safety shield accessory is worn by the dental patient below the eyewear worn by the dental patient.

16. The dental patient eyes safety shield accessory for eyewear as defined in claim 11, wherein:
- the first portion is folded into a plane approximately normal to a plane assumed by the deflector shield;
- the second portion is bendable from a first position thereof to a second position thereof, wherein the second portion, after being bent, retains the second position thereof and causes the first portion, after being bent with the second portion to bend from a first position thereof to a second position thereof that is also retained with the second position of the second portion;
- the first and second portions are bendable from the respective first positions thereof to the second positions thereof so as to be configured to make conforming fits over both:
  - the nose of the dental patient; and
  - the left and right cheek portions of the dental patient adjacent to the nose of the dental patient.

17. An eyes safety shield accessory for eyewear having left and right lenses and configured to be worn by a dental patient for protection of the eyes of the dental patient inherently exposed to aerosol sprays and flying air-borne fine-size particulate debris and projectiles from the uncovered oral cavity of the dental patient which may impact and harm the eyes of the dental patient during a dental care procedure provided by a dental professional, the accessory for eyewear comprising:
- a lower portion having a nose clip strip bendable to make the lower portion conformable to and in contact with:
  - the nose of a dental patient wearing the eyewear; and
  - left and right cheek portions adjacent to the nose of the dental patient wearing the eyewear; and
- an upper portion extending above the lower portion and having left and right regions each composed of polymeric material;

and ear loops configured to be fitted over or around the ears of the dental patient wherein the dental patient eyes safety shield accessory for eyewear is configured to be worn by the dental patient and overlaps the eyewear worn by the dental patient and is neither attached, connected, nor adhesively bound to the eyewear worn by the dental patient;

whereby:

when the ear loops are fitted over or around the ears of the dental patient, then the dental patient eyes safety shield accessory is held in place and against the face of the dental patient;

when the nose clip strip is positioned below left and right lenses of the eyewear:

the accessory for eyewear does not cover the oral cavity of the dental patient;

neither the lower portion nor the upper portion substantially block: the uncovered oral cavity; and the nostrils of the dental patient; and a line of vison of the dental patient wearing the eyewear; and the left and right regions respectively:

extend above a rectangular periphery of the lower portion to left and right lenses of the eyewear;

cover left and right gaps formed respectively:

between the left and right cheeks of the dental patient wearing the eyewear; and below left and right opposing sides of the eyewear, and deflect the aerosol sprays and the fling air-borne fine-size particulate debris and projectiles from the uncovered oral cavity of the dental patient which may impact and harm the eyes of the dental patient during the dental care procedure provided by the dental professional; the dental patient eyes safety shield accessory for eyewear does not cover the nostrils of the dental patient; and nothing is attached to a bottom or a posterior area of the dental patient eyes safety shield accessory for eyewear.

18. The eyes safety shield accessory for eyewear as defined in claim 17, wherein the upper portion is configured to be conformable to protect the eyes of the dental patient wearing the eyewear from:

perpendicular, frontal debris trajectory pathways; and side trajectory pathways.

\* \* \* \* \*